United States Patent
Cho et al.

(10) Patent No.: US 6,185,462 B1
(45) Date of Patent: Feb. 6, 2001

(54) APPARATUS FOR ELECTRICALLY TREATING SKIN DISORDERS

(75) Inventors: Casey Cho, La Canada, CA (US); Hur Joong Ki, Seoul (KR)

(73) Assignee: Innovative Medical Devices (UK) Ltd., Telford (GB)

( * ) Notice: Under 35 U.S.C. 154(b), the term of this patent shall be extended for 0 days.

(21) Appl. No.: 08/946,119

(22) Filed: Oct. 7, 1997

(30) Foreign Application Priority Data

Jan. 22, 1997 (KR) .................................................. 97-1774

(51) Int. Cl.⁷ ...................................................... A61N 1/20
(52) U.S. Cl. ............................. 607/75; 607/145; 607/147
(58) Field of Search ............................. 607/75, 145, 147, 607/150, 149, 151

(56) References Cited

U.S. PATENT DOCUMENTS

| 305,894 | * | 9/1884 | Clarke ................................... 607/145 |
| 493,723 | * | 3/1893 | Horton, Jr. ............................... 607/75 |
| 4,037,590 | * | 7/1977 | Dohring et al. ....................... 607/147 |
| 4,180,079 | * | 12/1979 | Wing ..................................... 607/151 |
| 5,090,402 | * | 2/1992 | Bazin et al. ............................ 601/17 |
| 5,133,352 | * | 7/1992 | Lathrop et al. ......................... 607/75 |
| 5,413,590 | | 5/1995 | Williamson . |
| 5,470,349 | * | 11/1995 | Kleditsch et al. ...................... 607/75 |
| 5,514,167 | * | 5/1996 | Smith et al. ............................ 607/75 |

FOREIGN PATENT DOCUMENTS

9004997 * 5/1990 (WO) .................................. 607/145

* cited by examiner

Primary Examiner—Kennedy Schaetzle
(74) Attorney, Agent, or Firm—Timothy Thut Tyson; Ted Masters; Freilich, Hornbaker & Rosen

(57) ABSTRACT

An apparatus for treating skin disorders includes a case, an electrode structure having a metal ball tip electrode for contacting the skin, and a metal electrode mounted on a handle portion of the electrode structure. The electrode structure can be conveniently grasped with one hand.

3 Claims, 2 Drawing Sheets

APPARATUS FOR ELECTRICALLY TREATING SKIN DISORDERS

BACKGROUND OF THE INVENTION

The present invention pertains generally to devices for treating skin disorders, and in particular to an apparatus which includes a metal ball tip electrode which is applied to a local area of the skin.

PRIOR ART

Treating facial skin disorders by using galvanic electric current is well known in the art. One such device is disclosed in U.S. Pat. No. 5,413,590 in which the treatment apparatus includes a conical electrode tip for treating localized skin disorders such as black heads and pimples. The skin treatment apparatus has a low voltage battery, including a negative pole connected to a probe having a metal electrode tip, and a positive pole connected to a metal plate which is mounted on a housing to be grasped by a user's hand. The metal plate forms a second electrode connected to the positive pole. The metal electrode tip has a pointed portion at an acute angle in the form of a circular cone of about 30°, thereby preventing the electrode tip from penetrating the skin.

However, since the electrodes of the aforementioned apparatus are separated, the user is inconvenienced by having to utilize two hands to operate the device. Also, the shape of the electrode is sharply pointed, and may not be safe when used by an unskilled person.

An object of the present invention is to provide an apparatus for electrically treating skin disorders which includes a metal ball tip which will not penetrate the skin, and an electrode structure which can be grasped with one hand.

SUMMARY OF THE INVENTION

An apparatus for electrically treating skin disorders comprises a case including a low voltage DC battery and a printed circuit board mounted therein for generating galvanic electricity. An electrode structure includes an electrode tip disposed on one end and connected to a negative pole, and a metal electrode connected to a positive pole. The electrode structure includes a body which is conveniently grasped with only one hand.

The electrode tip comprises a ball bearing such as is used in a ball point pen. The metal electrode is mounted on the body, and has a size and shape that can be contacted by a grasping hand. The printed circuit board includes a galvanic electric generating circuit for generating electric current. The ball tip prevents penetration of the skin when unskilled persons use the apparatus.

DETAILED DESCRIPTION OF THE INVENTION

Figure 1:
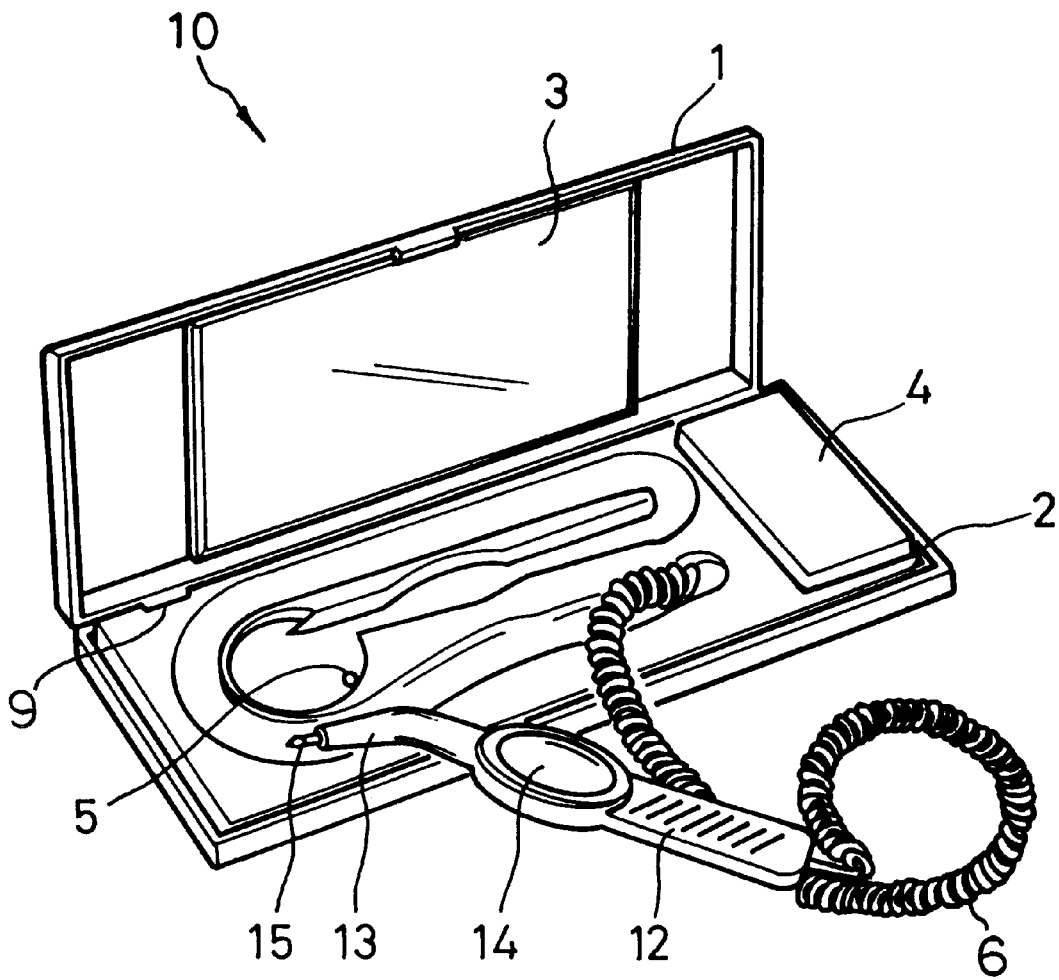
FIG. 1 is a perspective view illustrating an apparatus for treating skin disorders in accordance with the present invention.
Figure 3:
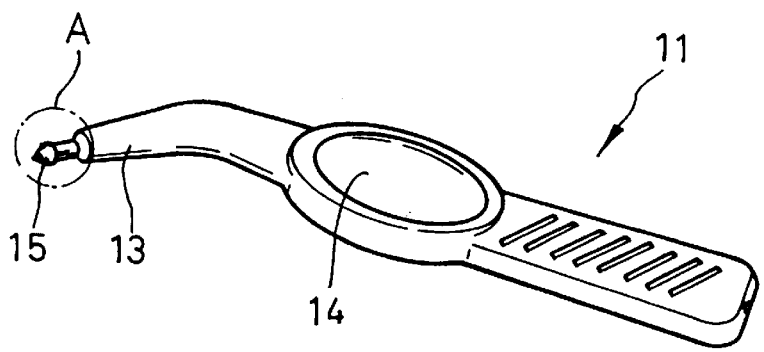
FIG. 3 is a perspective view highlighting the electrode tip portion of the invention; and, FIG. 4 is an enlarged view of area A of FIG. 3.
Figure 4:
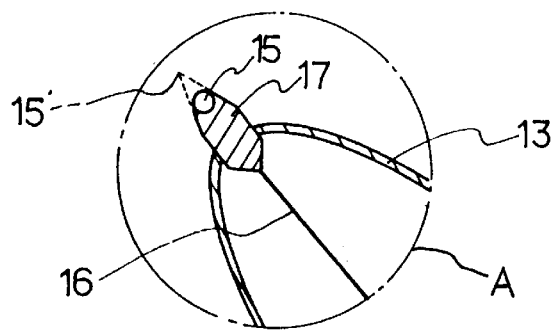

Referring to FIGS. 1, 3, and 4, the invention comprises a portable case 10 having a cover 1 coupled to a housing 2 by a hinge 9. Cover 1 includes an interior mounted mirror 3. Housing 2 includes a partition plate 4 for storing a battery and printed circuit board having a electric generating circuit for generating electric current (not shown) which are both disposed within case 10. An electric lead wire 6 connects an electrode structure 11 to the printed circuit board. A light emitting diode 5 is disposed upon position plate 4 to indicate that the apparatus is operating.

Electrode structure 11 includes a handle portion 12 and an extending portion 13 extending from handle portion 12. Extending portion 13 is hollow. Handle portion 12 has a side surface upon which is mounted a metal electrode 14. Metal electrode 14 comprises a plate which is connected to a positive portion of electrical lead wire 6.

Extending portion 13 includes an electrode tip 15 fixed at an end portion thereof. Electrode tip 15 is connected to a negative portion 16 of electrical lead wire 6. Electrode tip 15 includes a metal ball tip electrode similar to a ball bearing tip used in a ball point pen. Electrode tip 15 is tightly fixed, at an end of extending portion 13, to a metal supporter 17 to have a point crossed by two tangential lines 15' on the circular arc thereof, thereby forming an acute angle. The metal ball tip electrode is dimensioned so that it will not penetrate the skin during treatment of a local area.

Figure 2:
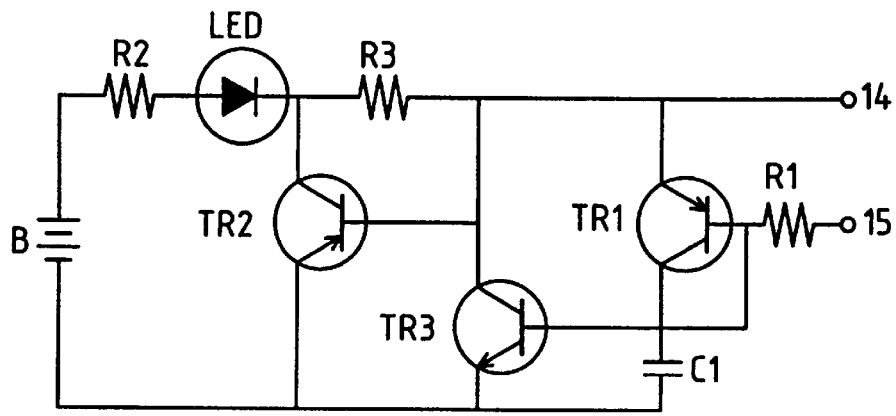
FIG. 2 is a circuit for operating the apparatus.

Referring now to FIG. 2, the galvanic electric generating circuit comprises a power source B (a low voltage battery), a switching transistor TR1, and a Darlington amplifier circuit including transistors TR2 and TR3 for amplifying current provided by power source B.

Power source B is connected at a positive pole to the anode of a light emitting diode (LED) via a resistor R2. The cathode of the light emitting diode is connected to the collector of transistor TR2. The emitter of transistor TR2 is connected to the negative pole of power source B. One side of a resistor R3 is connected to the cathode of the light emitting device and to the collector of transistor TR2. The opposite side of resistor R3 is connected to the base of transistor TR2, the collector of transistor TR3, the emitter of transistor TR1, and to metal electrode 14. Transistor TR2 is coupled with transistor TR3 to form the Darlington circuit, in which the base and emitter of transistor TR2 are respectively connected to the collector and emitter of transistor TR3. The emitters of transistors TR2 and TR3 are connected to the negative pole of power source B. The base of transistor TR3 is connected to the base of switching transistor TR1. The collector of switching transistor TR1 is connected via condenser C1 to the negative pole of power source B. The base of switching transistor TR1 is connected via resistor R1 to electrode tip 15. Condenser C1 removes parasitic alternating current, and floats switching transistor TR1 when the transistor is turned on.

Accordingly, the present invention enables users to grasp electrode structure 11 and thereby contact metal electrode 14, and then place electrode tip 15 upon an area of the skin. At that time switching transistor T1 is turned on. The Darlington circuit including transistors TR2 and TR3 amplifies the current of power source B, and the amplified current is supplied to electrode tip 15. Simultaneously, the light emitting diode turns on to indicate operation of the apparatus. Thereafter, when electrode tip 15 and metal electrode 14 are disconnected, transistor TR2 is turned off separating the positive and negative poles of power source B from each other.

What is claimed is:

1. Apparatus for treating skin disorders, comprising:
   an electrode structure;
   said electrode structure including a handle portion having a side surface;
   said electrode structure including an extending portion;
   a metal electrode mounted on said side surface of said handle portion; and,
   a metal ball tip electrode fixed to an end of said extending portion.

2. Apparatus according to claim 1, further including:
   a case including a cover coupled to a housing by a hinge;
   a printed circuit board for generating electric current disposed within said case;
   a battery disposed within said case; and,
   said electrode structure connected to said printed circuit board by a lead wire.

3. Apparatus according to claim 2, further including:
   said printed circuit board including an electric generating circuit;
   said electric generating circuit including means for switching said apparatus on and off; and,
   said electric generating circuit including means for amplifying current from a power source.

* * * * *